(12) United States Patent
Murray et al.

(10) Patent No.: US 8,609,873 B2
(45) Date of Patent: Dec. 17, 2013

(54) PROCESS FOR MAKING AND USING HOF.RCN

(75) Inventors: Christopher Murray, Reading (GB); Graham Sandford, Durham (GB)

(73) Assignee: The Secretary of State for Defense in Her Britannic Majesty's Government of the United Kingdom of Great Britain and Northern Ireland, Whitehall, London (GB)

( * ) Notice: Subject to any disclaimer, the term of this patent is extended or adjusted under 35 U.S.C. 154(b) by 420 days.

(21) Appl. No.: 12/675,852

(22) PCT Filed: Sep. 5, 2008

(86) PCT No.: PCT/GB2008/003018
§ 371 (c)(1),
(2), (4) Date: Oct. 19, 2010

(87) PCT Pub. No.: WO2009/030928
PCT Pub. Date: Mar. 12, 2009

(65) Prior Publication Data
US 2011/0040092 A1   Feb. 17, 2011

(30) Foreign Application Priority Data

Sep. 5, 2007  (GB) .................................. 0717237.2

(51) Int. Cl.
*C07D 301/12* (2006.01)
*C07D 205/06* (2006.01)
*C07D 209/90* (2006.01)

(52) U.S. Cl.
USPC ............................ 549/524; 568/704; 568/939

(58) Field of Classification Search
USPC .................................. 549/524; 568/704, 939
See application file for complete search history.

(56) References Cited

U.S. PATENT DOCUMENTS

2004/0258615 A1   12/2004   Buchanan et al.

FOREIGN PATENT DOCUMENTS

| EP | 1 358 931 A3 | 11/2003 |
|----|----|----|
| WO | WO 99/22857 | * 5/1999 |
| WO | WO 01/83466 | 11/2001 |

OTHER PUBLICATIONS

Dayan et al. (Tetrahedron 55 (1999) 3657-3664).*
Chambers et al. (J. Fluorine Chem. 2003, 119; p. 81-82.*
Roberge et al. (Chem. Eng. Technol. (2005), 28 (3); p. 318-323).*
Dayan et al. (Synthesis (1999), 1427-1430—Abstract).*
International Search Report for PCT/GB2008/003018, mailed Jan. 10, 2009.
Shawn, M. et al., "Oxidation of electron-deficient anilines by HOF. A route to nitro-containing compounds for molecular electronic devices", Organic Letters, vol. 2, No. 21, (Sep. 27, 2000), pp. 3405-3406.
Chambers, R.D. et al., "Microreactors for oxidations using fluorine", Journal of Fluorine Chemistry, vol. 119, No. 1, (Jan. 1, 2003), pp. 81-82.
Chambers et al, "Continuous Flow glassware reactors for the laboratory Synthesis of . . . ", Science Direct, Journal of Fluorine Chemistry, 128 (2007) 1439-1443.
Doku et al, "On-microchip multiphase chemistry—a review of microreactor . . .", Science Direct, Tetrahedron 61 (2005) 2733-2742.
Dirk et al, "Oxidation of Electron-Deficient Anilines by HOF. A Route to Nitro-Containing . . . ", Organic Letters, 2000, vol. 2, No. 21, 3405-3406; XP-002545035.
GB Search Report for GB 0717237.2 mailed Apr. 22, 2008.
International Preliminary Report on Patentability mailed Mar. 18, 2010 in PCT/GB2008/003018.
Dayan et al "An Efficient α-Hydroxylation of Carbonyls Using the HOF.CH₃CN Complex", Tetrahedron 55 (1999) 3657-3664.

* cited by examiner

*Primary Examiner* — Noble Jarrell
*Assistant Examiner* — Valerie Rodriguez-Garcia
(74) *Attorney, Agent, or Firm* — Nixon & Vanderhye P.C.

(57) ABSTRACT

The invention relates to a process for making HOF.RCN and using it to oxidise organic substrates in a quick and safe way. The process comprises passing diluted fluorine through a conduit and RCN in water through another conduit into a microreactor to form HOF.RCN and reacting this with an organic substrates.

14 Claims, 2 Drawing Sheets

PROCESS FOR MAKING AND USING HOF.RCN

This application is the U.S. national phase of International Application No. PCT/GB2008/003018 filed 5 Sep. 2008, which designated the U.S. and claims priority to Great Britain Application No. 0717237.2 filed 5 Sep. 2007, the entire contents of each of which are hereby incorporated by reference.

This invention relates to a process for making HOF.RCN in situ and a method of using it to effect reactions.

HOF is a known oxidising agent which is extremely unstable. Neat liquid HOF can be unpredictably explosive at temperatures greater than −40° C. It has been found that HOF can be rendered more stable by complexing it with acetonitrile. The resulting HOF.MeCN complex is relatively stable and is a very good oxygen transfer agent. Its oxygen atom, which comes from water, is bonded to the only element with a higher electronegativity which turns the oxygen into a strong electrophile. It is this permanent partially positive oxygen which enables HOF to behave as such an effective oxidising agent. As a result of the oxidation reaction, hydrofluoric acid (HF) is formed. The formation of the H—F bond is a strong driving force for the oxygen transfer process.

HOF.MeCN has been used to carry out the epoxidation of olefins, to effect the conversion of: aromatic amines to nitro arenes; aliphatic amines to nitro compounds; alcohols and methyl ethers to ketones; sulfides to sulfones; amino acids to α-nitro acids; and azides to nitro compounds. HOF.MeCN can be used in a batch process or a continuous process to oxidise substrates as detailed in the prior art.

With the batch process carried out in Organic Letters 2000, 2, 3405 by Tour, Dirk, Mickelson and Henderson not all of the fluorine reacted when it was bubbled through the wet acetonitrile. Also, fluorine gas accumulated in solution and accumulated in the vessel headspace where solvent vapour is present. Both of these situations may lead to a risk of explosion.

Further, the known batch process is difficult or impossible to scale beyond a certain point due to the finite time needed to generate a large quantity of HOF reagent. Additionally, the accumulation of a large volume of such an unstable reagent could present a safety risk.

In the Tour, Dirk et al publication it was reported that it was necessary to form HOF.MeCN at minus 20° C. and it must be used at similarly low temperatures due to stability issues, as higher temperatures cause significant HOF decomposition. However, low temperature conditions require longer reaction times and this may result in either decomposition of RCN or further undesirable reaction of the starting materials or products. As there is not precise control over the reagent feed and reactor conditions, and hence conversion of fluorine to HOF.MeCN, titrations of HOF.MeCN solution need to be performed and this is a hazardous step.

In order to convert aliphatic amines to nitro compounds, an HF scavenging agent, such as sodium fluoride, NaF, needs to be used to enable oxidation to occur. Product mixtures resulting from oxidation reactions contain HF and the manipulation of such mixtures is potentially hazardous.

Another process used to carry out oxidation of substrates with HOF.MeCN is a continuous process. The procedure described in the Journal of Fluorine Chemistry, 2003, 119, 81 by Chambers et al. does not work for most substrates due to the reactivity of them with fluorine. For simple substrates such as alkenes or amines this is a major problem as extensive fluorination and/or decomposition of the substrate will occur. Further, the use of formic acid as a solvent for the HOF is potentially dangerous/undesirable due to the use of large quantities of this corrosive material. The resulting solution of HOF in formic acid is unstable and corrosive which leads to a more hazardous process.

The present invention seeks to overcome these problems by providing a process for making and a method of using HOF.RCN which is far quicker and safer than the prior art.

The highly reactive nature of HOF.RCN allows for the use of a microreactor system for the continuous synthesis of HOF.RCN and the continuous oxidation of a substrate or substrates, thus minimising hazardous inventory, hazardous materials handling and maximising process efficiency with minimal operator effort. The unstable nature of HOF.MeCN with a half-life of about 4 hours at 20° C. means that such continuous generation techniques are beneficial for synthesis at any scale.

The invention comprises a process for oxidising substrates using HOF.RCN using an apparatus comprising at least: a first conduit and a second conduit linked to a first end of at least one channel in a microreactor, a third conduit attached to a second end of the at least one channel, the third conduit terminating in a pot reactor. The process comprises passing diluted fluorine through a conduit into a microreactor channel, passing RCN in water through another conduit thereby forming HOF.RCN, and contacting the HOF.RCN with a substrate to be oxidised, wherein the HOF.RCN formation and oxidation stages are decoupled within the same reaction system thereby allowing the continuous generation of HOF.RCN.

This ensures that no fluorine comes into contact with the substrate and therefore the process can be applied to substrates that contain functionalities which are reactive towards fluorine. Such substrates include but are not limited to: aliphatic and aromatic amines, alkenes, N-heterocycles, azides, activated carbonyl compounds, esters and hydrocarbons.

The process for oxidising a substrate using the apparatus described above comprises: passing diluted fluorine through a conduit into a microreactor channel, passing RCN in water through a conduit, and contacting the mixture with a substrate to be oxidised, wherein the HOF.RCN formation and oxidation stages are decoupled within the same reaction system thereby allowing the continuous generation of HOF.RCN.

The process of the invention can be a semi-batch process or a continuous process which comprises continuous generation of HOF.RCN, with continuous injection of the substrate solution into the microreactor in the continuous process.

HOF.RCN is made in this invention in the preferential method of the prior art where a stream of RCN in or containing water is brought into contact with diluted fluorine.

In the process of the invention all of the fluorine is converted to HOF so there is no explosion risk and there is therefore efficient use of fluorine gas. As all of the fluorine is consumed prior to reaching any vessel where flammable vapours could accumulate in the headspace, the risk of explosion is mitigated. In addition, the consumption of all the fluorine prevents the potentially hazardous accumulation of fluorine in solution following the HOF.RCN formation step. The process can be scaled up by using additional identical reaction channels either in the same reaction block or in one or more separate microreactors, and the dimensions of the channels may be altered if required. It is preferable to carry out the process in the block reactor so that the flow rates of the substrates input are constant and the same throughout the reaction.

This process, where the HOF.RCN is generated continuously, allows for the heating of the oxidation zone of the reactor, thus providing the ability to oxidise difficult substrates more efficiently. Cooling the HOF.RCN formation zone to temperatures appreciably below 20° C. is not necessary. Temperature control is not always needed on a small scale during HOF.RCN formation.

There is a minimal inventory of fluorine and HOF at any one time which increases the safety level of the process. Hazardous titrations of HOF.MeCN solution are not needed due to the precise control over reagent feed and reactor conditions. The reagent feed may be controlled by a gas flow meter or any other suitable means. The liquid flow may be controlled by a syringe or any other metering pump. The path length can be optimised, for example by measuring residence times, to ascertain the optimum path length, based on the yields of recovered materials or any suitable on-process analytical technique. The microreactor has a path whereby it can be heated or cooled depending upon what is required which results in excellent heat transfer in the microreactor. A HF scavenging agent is not needed to oxidise aliphatic amines to nitro compounds which allows the process to be continuous. The process also allows for direct quenching of the reaction which means that there is no danger of handling HF when manipulating the product mixtures.

The process lends itself to scaling out the process as the microreactor increases the efficiency and reduces the need for safety critical cooling due to there being excellent heat transfer in the microreactor. Adding additional channels or reactors allows for scale-out of the process whilst maintaining the same safety or process parameters as in a single channel, in contrast to batch scale-up processes.

This process, when operated in semi-batch mode, allows for the oxidation of poorly soluble or insoluble substrates with continuously generated HOF.RCN as the substrate is located in a pot reactor into which HOF.RCN mixture is fed.

The substrate may be present during HOF.RCN generation in the semi-batch process or added after. An HF scavenger (e.g. NaF) may be added if the substrate is acid sensitive.

Semi-Batch Process:

The semi-batch process of the invention gives control over the flow rates to ensure complete consumption of fluorine in the HOF.RCN formation step. With existing single channel systems the use of cooling is unnecessary. However, scaling out the process by including a number of channels might require the use of a cooing fluid to be passed through the microreactor. Quenching is effected by passing the flow into a solution, e.g. $NaHCO_3$. This removes the health and safety issues seen in the published processes associated with HF handling when manipulating the product mixtures. The HOF.RCN may be passed into a stirred tank or other reactor containing a solution of substrate. This minimises inventory of both fluorine and HOF.RCN. Alternatively, the substrate may be added following HOF.RCN generation. This allows for the oxidation of substrates which are unstable to extended exposure to HF (a by-product) or which require only a short contact time with HOF before decomposition or further reaction, whilst minimising the inventory of fluorine in the system.

Continuous:

The continuous process of the invention gives control over the flow rates to ensure complete consumption of fluorine in the HOF.RCN formation step. The reagent feed may be controlled by a gas flow meter or any other suitable means. The liquid flow may be controlled by a syringe or any other metering pump. Again, the path length can be optimised as described above. The microreactor has a path whereby it can be heated or cooled depending upon what is required which results in excellent heat transfer in the microreactor.

The HOF.RCN solution may be fed into a second continuous stage, potentially in the same flow reactor, into which an oxidisable substrate or a solution of oxidisable substrate is injected. The solvent used for the substrate can then include those which are not compatible with fluorine as all of the fluorine is consumed which is unique to the process of the invention. Solvent mixtures, for example MeCN/DCM, can also be used as carrier phases for the substrates, including solvents which are reactive towards fluorine, such as dichloromethane (DCM).

The continuous method of the invention allows for the quicker and safer oxidation of at least primary and tertiary aliphatic amines, aromatic amines, aliphatic azides, alkenes and azaheterocycles compared with the prior art. It also allows for much easier scale-up of the process and does not require the use of a heterogeneous acid scavenger such as NaF for the oxidation of aliphatic amines.

Additional microreactors or additional channels on the same reactor allow for safe process scale out overcoming the traditional difficulties associated with the scale up of exothermic batch reactions such as oxidation. Where two microreactors are used the first performs the HOF formation whilst the second performs the substrate oxidation. Fortunately, full independent temperature control can be achieved if required by passing a heating or cooling fluid through the microreactor block. It may be necessary to cool the microreactor block during the formation of HOF.RCN with larger numbers of channels or to heat the microreactor block if the oxidation stage is slow.

These processes are applicable to any chemical process requiring oxidation amenable to HOF.RCN chemistry providing substrates and products are soluble in the process solvent(s) (for the continuous process). This process is particularly suitable for substrates which are resistant to conventional oxidation techniques or for which more environmentally friendly, heavy metal free techniques are required. This process is suitable for scale up so that oxidations can be carried out on large volumes of substrates. The resulting products may be of use in, for example, energetic materials, pharmaceuticals and fine chemicals.

The apparatus used in the invention allows for safe handling of the materials, overcoming the health and safety problems associated with the prior art. It also leads to quicker reaction times, typically from less than a second to several seconds. These times are considerably faster than those known in the prior art and produce similar yields. A sequential reaction could be used, for example having one reactor making HOF.RCN with a substrate injection, and then feeding in this partially oxidised stream as the substrate to a second reactor with more HOF.RCN formation. Alternatively the feed rates and conditions could be optimised by any known method to increase the yield in the single reactor.

The apparatus comprises various conduits through which the diluted fluorine, RCN in water and possibly the substrate to be oxidised are passed. Some or all of these will go into the microreactor where the fluids can mix to form the final product, form HOF.RCN or simply just be cooled or heated.

The microreactor is linked to a pot reactor by a conduit to collect the products in the continuous process. In the semi-batch process the pot reactor may contain a solution of the substrate to be oxidised or RCN and the substrate to be oxidised is added to this. In the continuous process, where the pot reactor collects the product, it may also contain a quench solution to neutralise the HOF.RCN and HF formed. The pot reactor may be cooled. It is preferably made of a fluoropolymer material or any other material which will not be affected by HF, fluorine, HOF or the other reaction chemicals.

Additionally, the apparatus may comprise a cooled catch pot which will collect any hazardous volatiles. It is merely a piece of safety equipment should there be any traces of these materials. The catch pot can be connected to a soda lime scrubber via a conduit. The soda lime scrubber destroys any residual fluorine or hydrofluoric acid. It is unlikely that either of these will get through; the scrubber is merely another safety device.

The invention will now be further described with reference to the accompanying drawings.

FIG. 1 is a schematic of the apparatus used in the semi-batch process where HOF. RCN is continuously generated.

Figure 1:
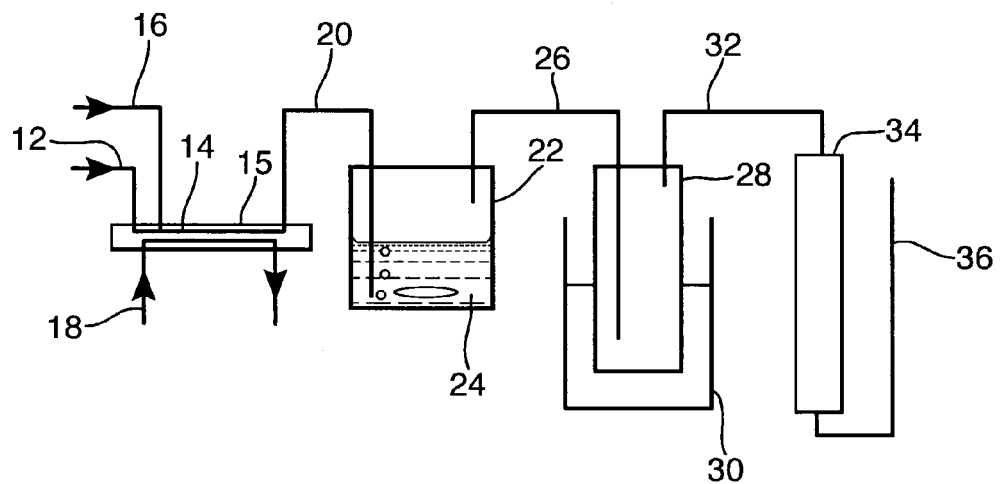
FIG. 1 shows a preferred apparatus set up for a semi-batch process.

A first conduit 12 feeds into the start of a first channel 14 in a microreactor 15. A second conduit 16 joins the channel 14 along its length. The microreactor block 15 has a second channel 18 through which heating or cooling fluids flow. The channel 14 is connected via a third conduit 20 to a pot reactor 22 which contains a solution of the substrate 24 to be oxidised or RCN if the substrate is to be added later. The pot reactor 22 is linked to a catch pot 28 by a fourth conduit 26. The catch pot 28 is cooled in an ice bath 30. The catch pot 28 is linked to a soda lime scrubber 34 by a fifth conduit 32. A sixth conduit 36 extends from the soda lime scrubber 34 to the atmosphere Dilute, preferably 10%, fluorine in nitrogen is fed into the microreactor channel 14 through the first conduit 12 and RCN and water mixture is fed into the channel 14 in the microreactor block 15 via the second conduit 16 to form HOF.RCN in the microreactor 15. The HOF.RCN is transferred into the pot reactor 22 where there is already a solution of the substrate 24 to be oxidised. Alternatively, the pot reactor 22 contains RCN into which the HOF.RCN will flow and the substrate to be oxidised is added after the HOF.RCN generation. The reaction products collect in the pot reactor 22, and can be isolated using any applicable known technique, for example solvent extraction followed by drying and evaporation of the extraction solvent. A catch pot 28 is employed to collect any hazardous volatiles which come from the pot reactor 22 through the fourth conduit 26 although none is expected to collect here, it is merely a safety feature. A soda lime scrubber 34 is used to destroy any residual fluorine or HF which is transferred from the catch pot 28 via the fifth conduit, although this again is a safety device as no residual materials are expected to collect.

Alternatively, fluorine in nitrogen can be fed into the microreactor via second conduit 16 and the RCN/H$_2$O mixture can be fed through the first conduit 12.

Figure 2:
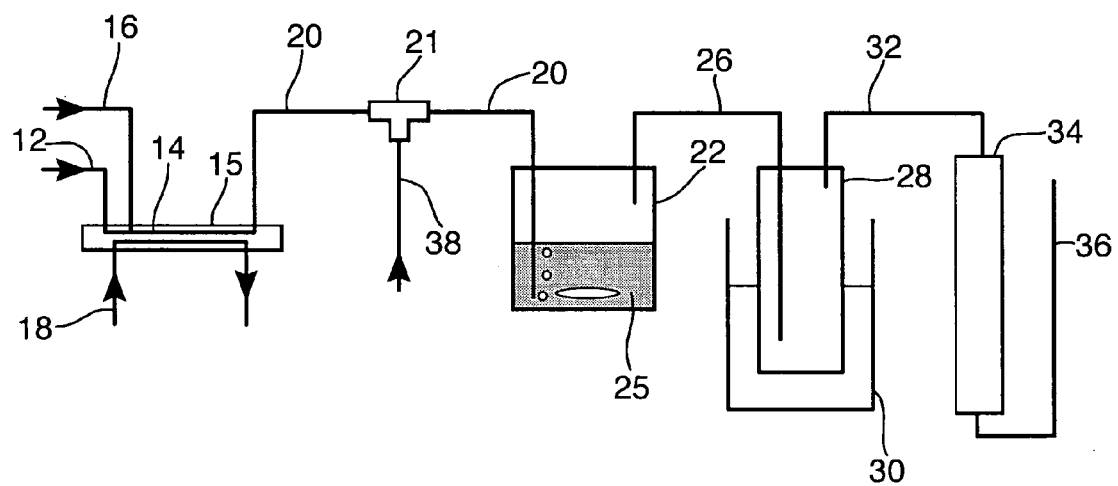
FIG. 2 shows a first preferred apparatus set up for a continuous mode process.

FIG. 2 is a schematic of a first preferred embodiment of the apparatus used in a continuous mode process. A first conduit 12 feeds into the start of a channel 14 in the microreactor 15. A second conduit 16 joins the channel 14 along its length. The microreactor block has another channel 18 through which heating or cooling fluids flow. The channel 14 is connected via a third conduit 20 to a pot reactor 22. The third conduit 20 has a T-piece 21 along its length which has a seventh conduit 38 attached to it. The pot reactor 22 is linked to a catch pot 28 by a fourth conduit 26. There is a quench solution 25 in the pot reactor 22. The catch pot 28 is cooled in an ice bath 30. The catch pot 28 is linked to a soda lime scrubber 34 by a fifth conduit 32. A sixth conduit 36 extends from the soda lime scrubber 34 to atmosphere.

HOF.RCN is generated continuously by feeding RCN/H$_2$O through the first conduit 12 into the channel 14 in the microreactor 15 and dilute, preferably 10%, fluorine in nitrogen through the second conduit 16 into the channel 14. This forms HOF.RCN in the microreactor 15 which flows from the microreactor 15 to the pot reactor 22 via the third conduit 20. A solution of the substrate to be oxidised 24 (not shown) is continuously fed through the seventh conduit 38 and through the T-piece 21 into the third conduit 20 to react with the HOF.RCN. The reaction products collect in the pot reactor 22. The pot reactor 22 may contain a quench solution 25 to neutralise the HOF.RCN and HF. The reactions products collect in the pot reactor 22 and can be isolated using any applicable known technique, for example solvent extraction followed by drying and evaporation of the extraction solvent. A catch pot 28 is employed to collect any hazardous volatiles which come from the pot reactor 22 through the fourth conduit 26 although none is expected to collect here, it is merely a safety feature. A soda lime scrubber 34 is used to destroy any residual fluorine of HF which is transferred from the catch pot 28 via the fifth conduit, although this again is a safety device as no residual materials are expected to collect.

Alternatively, fluorine in nitrogen can be fed into the microreactor via first conduit 12 and the RCN/H$_2$O mixture can be fed through the second conduit 16.

Figure 3:
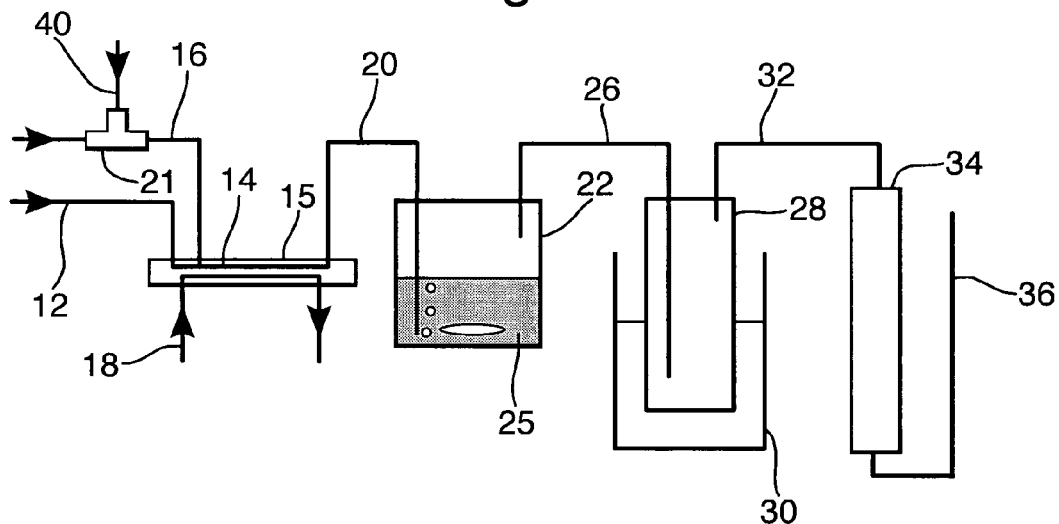
FIG. 3 shows a second preferred apparatus set up for a continuous mode process.

FIG. 3 is a schematic of a second preferred embodiment of the apparatus used in a continuous mode process. A first conduit 12 feeds into the start of a channel 14 in the microreactor 15. A second conduit 16 joins the channel 14 along its length. This second conduit 16 has a T-piece 21 along its length which has an eighth conduit 40 attached to it. The microreactor block 15 has another channel 18 through which heating or cooling fluids flow. The channel 14 is connected via a third conduit 20 to a pot reactor 22. The pot reactor 22 is linked to a catch pot 28 by a fourth conduit 26. There is a quench solution 25 in the pot reactor 22. The catch pot 28 is cooled in an ice bath 30. The catch pot 28 is linked to a soda lime scrubber 34 by a fifth conduit 32. A sixth conduit 36 extends from the soda lime scrubber 34 to atmosphere.

A solution of the substrate to be oxidised 24 (not shown) is fed through the first conduit 12 into the channel 14 in the microreactor 15. Dilute, preferably 10%, fluorine in nitrogen is fed through the second conduit 16 and comes into contact with RCN/H$_2$O fed through the eighth conduit 40 and the T-piece 21 into the second conduit 16. The stream of the resulting products flows into the channel 14. The oxidised substrate and other products flow from the microreactor 15 to the pot reactor 22 via the third conduit 20. The pot reactor may contain a quench solution 25 to neutralise the HOF.RCN and HF. The reactions products collect in the pot reactor 22 and can be isolated by any applicable known technique, for example solvent extraction followed by drying and evaporation of the extraction solvent. A catch pot 28 is employed to collect any hazardous volatiles which come from the pot reactor 22 through the fourth conduit 26 although none is expected to collect here, it is merely a safety feature. A soda lime scrubber 34 is used to destroy any residual fluorine of HF which is transferred from the catch pot 28 via the fifth conduit, although this again is a safety device as no residual materials are expected to collect. The substrate solution can be preheated using this apparatus before it comes into contact with the oxidant.

Alternatively, fluorine in nitrogen can be fed into the microreactor via the eight conduit 40 and the RCN/H$_2$O mixture can be fed through the second conduit 16.

Figure 4:
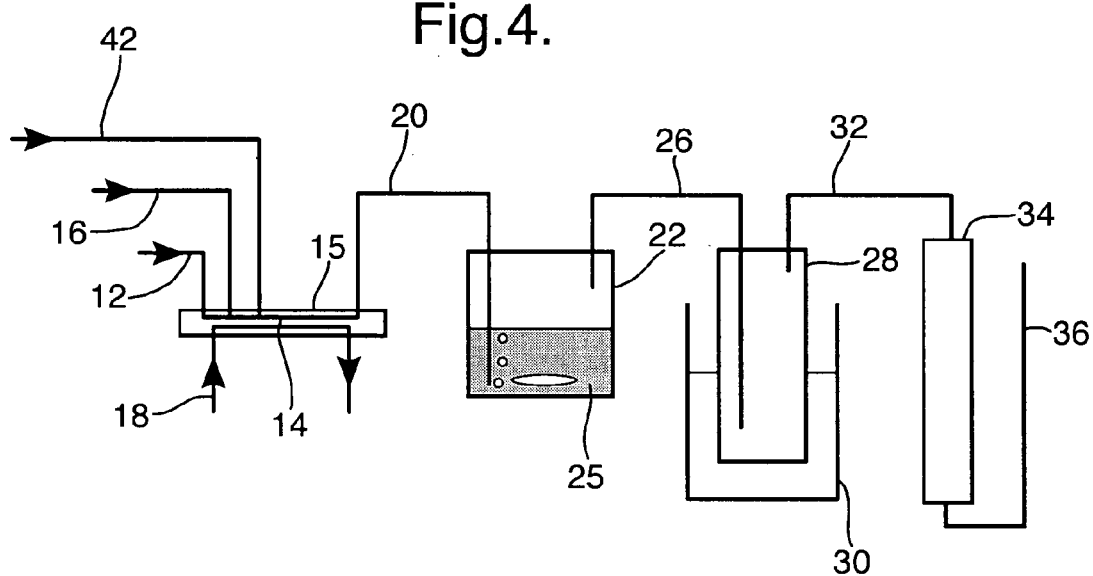
FIG. 4 shows a third preferred apparatus set up for a continuous mode process

FIG. 4 is a schematic of a third preferred embodiment of the apparatus used in a continuous mode process. A first conduit 12 feeds into the start of a channel 14 in the microreactor 15. A second conduit 16 joins the channel 14 along its length. A ninth conduit 42 also connects with the channel 14 further along its length than the second conduit 16. The microreactor block 15 has another channel 18 through which heating or cooling fluids flow. The channel 14 is connected via a third conduit 20 to a pot reactor 22. The pot reactor 22 is linked to a catch pot 28 by a fourth conduit 26. There may be a quench solution 25 in the pot reactor 22. The catch pot 28 is cooled in an ice bath 30. The catch pot 28 is linked to a soda lime scrubber 34 by a fifth conduit 32. A sixth conduit 36 extends from the soda lime scrubber 34 to atmosphere.

HOF.RCN is generated continuously by feeding dilute, preferably 10%, fluorine in nitrogen through the first conduit 12 into the channel 14 in the microreactor 15 and RCN/H$_2$O through the second conduit 16 into the channel 14. This forms HOF.RCN in the microreactor 15. A solution of the substrate to be oxidised 24 (not shown) is fed through a ninth conduit 42 which also flows into the channel 14. HOF.RCN is generated in the microreactor 15 before the substrate solution 24 is added. The reaction products flow from the microreactor 15 to the pot reactor 22 via the third conduit 20. The reaction products collect in the pot reactor 22 and may be isolated by any applicable known technique, for example solvent extraction followed by drying and evaporation of the extraction solvent. The pot reactor 22 may contain a quench solution to neutralise the HOF.RCN and HF. A catch pot 28 is employed to collect any hazardous volatiles which come from the pot reactor 22 through the fourth conduit 26 although none is expected to collect here, it is merely a safety feature. A soda lime scrubber 34 is used to destroy any residual fluorine of HF which is transferred from the catch pot 28 via the fifth conduit, although this again is a safety device as no residual materials are expected to collect.

Alternatively, fluorine in nitrogen can be fed into the microreactor via second conduit 16 and the RCN/H$_2$O mixture can be fed through the first conduit 12.

It is clear from the description of the figures that the apparatus of FIG. 4 could be modified to operate with two or more reactor blocks with sequential generation and addition of HOF. The inventor has successfully trialled the use of two reactor blocks. The first block performed the HOF.RCN formation whilst the second performed the substrate oxidation. Full independent temperature control of each microreactor block is achievable.

Results

All of the products were identified and confirmed by spectroscopic techniques and were in agreement with the literature.

Semi-Batch Process

The following reactions were carried out using the apparatus shown in FIG. 1, 2-decyloxirane from 1-dodecene

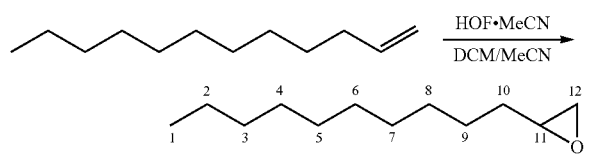

Under a flow of F$_2$ (10% in N$_2$) of 8.9 ml min$^{-1}$ (1.49 mmol h$^{-1}$) fed through conduit 12, MeCN:H$_2$O (4:1, 5.50 ml) was added to conduit 16 at a rate of 5.50 ml$^{-1}$ (60.4 mmol h$^{-1}$). A solution of dodec-1-ene 24 (0.25 g, 1.49 mmol) (in a 1:1 mixture of DCM:MeCN) was added to pot reactor 22 prior to reaction. The HOF.MeCN thus generated was passed via conduit 20 into the pot reactor 22. Following reaction and purging with nitrogen, the reaction mixture was then transferred from pot reactor 22 to a vessel containing 100 ml of sodium bicarbonate solution, washed with DCM (3×75 ml), dried over MgSO$_4$ and filtered. The solvent was removed under reduced pressure to yield 2-decyloxirane (0.233 g, 1.27 mmol, 85%) as a pale yellow oil, with no further purification required.

$\nu_{max}$ (cm$^{-1}$) 2923(sp$^3$ C—H), 2854 (sp$^3$ C—H), 1466, 916, 833 (C—O—C), 722; $\delta_H$ (400 MHz, CDCl$_3$) 0.86 (3H, t, $^3J_{HH}$ 6.4, —CH$_2$CH$_3$), 1.24 (15H, m, —CH$_2$—), 1.47 (3H, m, —CH$_2$—), $\delta_C$ (100 MHz, CDCl$_3$) 14.0 (1C, s, C$_1$), 22.6 (1C, s, C$_2$), 25.9 (1C, s, C$_9$), 29.3, 29.4, 29.5, 29.6, 31.9 (5C, s, C$_{4-8}$), 32.4 (1C, s, C$_3$), 32.5 (1C, s, C$_{10}$), 47.0 (1C, s, C$_{12}$), 52.3 (1C, s, C$_{11}$); m/z (EI) 184 (M$^+$, 2%), 169 (M$^+$-CH$_3$, 100%).

Nitrobenzene from Phenylamine

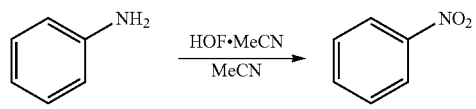 [SMILES: "MeCN" ; Nc1ccccc1 ; O=[N+]([O-])c1ccccc1]

According to the method above, phenylamine was reacted with 3.3 equivalents of HOF, with substrate 24 addition following HOF.MeCN generation, to yield 94% of nitrobenzene.

Similar yields, within 3-4%, were obtained when the substrate was added before HOF.RCN generation and during HOF.RCN generation, proving that fluorine was consumed completely by the HOF.RCN formation step.

Continuous

The following reactions were carried out using the apparatus shown in FIG. 2.

Alkenes 2-decyloxirane from 1-dodecene

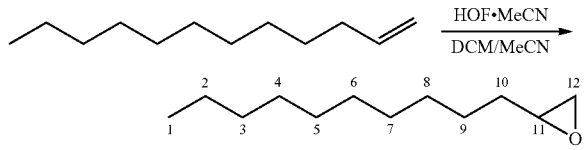

Under a flow of F$_2$ (10% in N$_2$) of 20.0 ml min$^{-1}$ (3.33 mmol h$^{-1}$) passed through conduit 12, MeCN:H$_2$O (4:1, 4.95 ml) was added to conduit 16 at a rate of 9.90 ml h$^{-1}$ (110.0 mmol h$^{-1}$) and dodec-1-ene 24 (0.18 g, 1.07 mmol) (in a 1:1 mixture of DCM:MeCN) was added to conduit 38 at a rate of 9.90 ml h$^{-1}$. All reaction fluids were collected in pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield 2-decyloxirane (0.195 g, 1.06 mmol, 99%) as a yellow oil, with no further purification required.

$v_{max}$ (cm$^{-1}$) 2923(sp$^3$ C—H), 2854 (sp$^3$ C—H), 1466, 916, 833 (C—O—C), 722; δ$_H$ (400 MHz, CDCl$_3$) 0.86 (3H, t, $^3J_{HH}$ 6.4, —CH$_2$CH$_3$), 1.24 (15H, m, —CH$_2$—), 1.47 (3H, m, —CH$_2$—), δ$_C$ (100 MHz, CDCl$_3$) 14.0 (1C, s, C$_1$), 22.6 (1C, s, C$_2$), 25.9 (1C, s, C$_9$), 29.3, 29.4, 29.5, 29.6, 31.9 (5C, s, C$_{4-8}$), 32.4 (1C, s, C$_3$), 32.5 (1C, s, C$_{10}$), 47.0 (1C, s, C$_{12}$), 52.3 (1C, s, C$_{11}$); m/z (EI) 184 (M$^+$, 2%), 169 (M$^+$-CH$_3$, 100%).

trans-2,3-diphenyloxirane from trans-stilbene

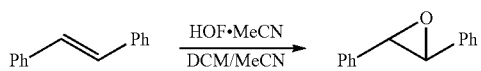

Under a flow of F$_2$ (10% in N$_2$) of 20.0 ml min$^{-1}$ (3.33 mmol h$^{-1}$) passed through first conduit 12, MeCN:H$_2$O (4:1, 4.95 ml) was added to conduit 16 at a rate of 9.90 ml h$^{-1}$ (110.0 mmol h$^{-1}$) and trans-stilbene 24 (0.36 g, 2.0 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield trans-2,3-diphenyloxirane (0.39 g, 1.99 mmol, 99%) as a yellow solid, with no purification required;

$v_{max}$ (cm$^{-1}$) 2989 (sp$^3$ C—H), 1493, 1425, 846 (C—O—C), 746, 696; δ$_H$ (400 MHz, CDCl$_3$) 3.95 (2H, s, OCH), 7.43 (10H, m, —CH—); δ$_C$ (100 MHz, CDCl$_3$) 61.1 (2C, s, epoxide C's), 123.8, 126.6, 126.9, 135.4 (12C, s, Ar C's); m/z (EI) 196 (M$^+$, 38%), 195 (M$^+$-H, 52%).

cis-2,3-diphenyloxirane from cis-stilbene

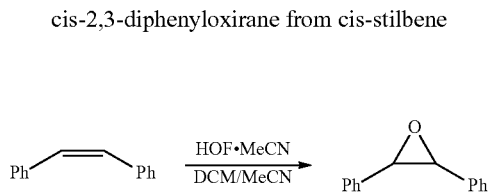

Under a flow of F$_2$ (10% in N$_2$) of 20.0 ml min$^{-1}$ (3.33 mmol h$^{-1}$) passed through first conduit 12 MeCN:H$_2$O (4:1, 4.95 ml) was added to second conduit 16 at a rate of 9.90 ml h$^{-1}$ (110.0 mmol h$^{-1}$) and cis-stilbene 24 (0.18 g, 1.00 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield a mixture of 3 products (confirmed by GC) (0.19 g) as a red oil, which included cis-2,3-diphenyloxirane (0.16 g, 0.81 mmol, 81%); δ$_H$ (400 MHz, CDCl$_3$) 4.38 (2H, s, OCH), 7.18 (10H, m, —CH—); δ$_C$ (100 MHz, CDCl$_3$) 59.8 (2C, s, epoxide C's), 126.9, 127.5, 127.8, 134.4 (12C, s, Ar C,s); m/z (EI) 196 (M$^+$, 44%), 195 (M$^+$-H, 64%).

1a,2,3,7b-tetrahydronaphtho[1,2-b]oxirene from 1,2-dihydronaphthalene

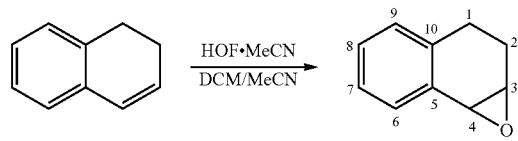

Under a flow of F$_2$ (10% in N$_2$) of 20.0 ml min$^{-1}$ (3.33 mmol h$^{-1}$) fed through first conduit 12, MeCN:H$_2$O (4:1, 4.95 ml) was added to conduit 16 at a rate of 9.90 ml h$^{-1}$ (110.0 mmol h$^{-1}$) and 1,2-dihydronaphthalene 24 (0.13 g, 1.00 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield a mixture of 6 products (confirmed by GC) (0.15 g) as a dark red oil, which included 1a,2,3,7b-tetrahydronaphtho[1,2-b]oxirene (0.12 g, 0.82 mmol, 82%);

δ$_H$ (400 MHz, CDCl$_3$) 1.64 (1H, m), 2.29 (1H, m), 2.43 (1H, m), 2.67 (1H, m), 3.61 (1H, t, $_3J_{HH}$ 4, C$_3$), 3.72 (1H, d, $^3J_{HH}$ 4, C$_4$), 6.97 (1H, d, $^3J_{HH}$ 8, C$_9$), 7.11 (2H, m, C$_{7,8}$) 7.27 (1H, d, $^3J_{HH}$ 8, C$_6$); δ$_C$ (100 MHz, CDCl$_3$) 21.8 (1C, s, C$_2$), 24.4 (1C, s, C$_1$), 52.8 (1C, s, C$_3$), 55.1 (1C, s, C$_4$), 126.1, 128.4, 128.5, 129.6 (4C, s, C$_{6-9}$), 132.6, 136.7 (2C, s, C$_{5,10}$); m/z (EI) 146 (M$^+$, 28%), 145 (M$^+$-H, 38%), 130 (M$^+$-O), 115 (M$^+$-CH$_3$O, 75%), 91 (M$^+$-C$_3$H$_4$O, 55%).

1,5-dioxatricyclodecane from 1,5-cyclooctadiene

Under a flow of F$_2$ (10% in N$_2$) of 20.0 ml min$^{-1}$ (3.33 mmol h$^{-1}$) passed through first conduit 12, MeCN:H$_2$O (4:1, 4.95 ml) was added to conduit 16 at a rate of 9.90 ml h$^{-1}$ (110.0 mmol h$^{-1}$) and 1,5-cyclooctadiene 24 (0.11 g, 1.02 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield a mixture of 3 products (confirmed by GC) (0.14 g) as a clear oil, which included 1,5-dioxatricyclodecane (0.13 g, 0.96 mmol, 94%);

δ$_H$ (400 MHz, CDCl$_3$) 1.88 (10H, m, —CH$_2$—), 2.92 (3H, t, $^3J_{HH}$ 4, OCH), δ$_C$ (100 MHz, CDCl$_3$) 21.9 (4C, s, C$_2$), 56.0 (4C, s, C$_1$); m/z (EI) 141 (MH$^+$, 26%) 140 (M$^+$, 34%).

ethyl 2-(3-ethyloxiran-2-yl)acetate from ethyl trans-3-hexanoate

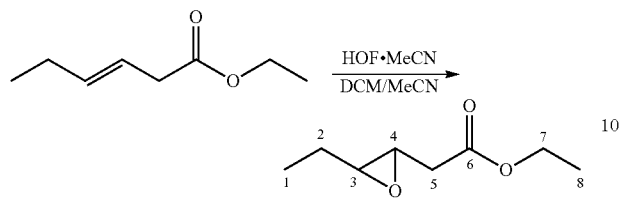

Under a flow of $F_2$ (10% in $N_2$) of 20.0 ml min$^{-1}$ (3.33 mmol h$^{-1}$) passed through first conduit 12, MeCN:$H_2O$ (4:1, 4.95 ml) was added to conduit 16 at a rate of 9.90 ml h$^{-1}$ (110.0 mmol h$^{-1}$) and ethyl trans-3-hexenoate 24 (0.14 g, 0.98 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield ethyl-2-(3-ethyloxiran-2-yl) acetate (0.15 g, 0.95 mmol, 97%) as a clear oil, with no further purification required; $v_{max}$ (cm$^{-1}$) 2973 (sp$^3$ C—H), 1734 (C=O), 1253, 1180, 1028, 887 (C—O—C); $\delta_H$ (400 MHz, CDCl$_3$) 0.98 (3H, t, $^3J_{HH}$ 8, H$_1$), 1.26 (3H, t, $^3J_{HH}$ 8, H$_8$), 1.58 (2H, quin, $^3J_{HH}$ 8, H$_2$), 2.53 (2H, d,d, $^3J_{HH}$ 8, H$_5$), 4.16 (2H, q, $^3J_{HH}$ 8, H$_7$), 2.72 (1H, t,d, $^3J_{HH}$ 8, $^3J_{HH}$ 4, H$_3$), 3.03 (1H, t,d, $^3J_{HH}$ 4, H$_4$); $\delta_C$ (100 MHz, CDCl$_3$) 9.7 (1C, s, C$_1$), 14.1 (1C, s, C$_8$), 24.8 (1C, s, C$_2$), 37.8 (1C, s, C$_5$), 53.7 (1C, s, C$_4$), 59.6 (1C, s, C$_3$), 60.8 (1C, s, C$_7$), 170.4 (1C, s, C$_6$); m/z (EI) 159 (MH$^+$, 2%).

Methyl 3-ethyl-2-methyloxirane-2-carboxylate from methyl trans-2-methyl pentanoate

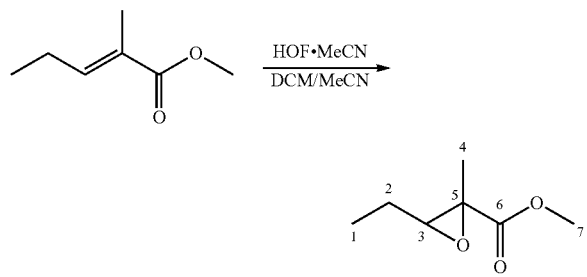

Under a flow of $F_2$ (10% in $N_2$) of 20.0 ml min$^{-1}$ (3.33 mmol h$^{-1}$) passed through first conduit 12, MeCN:$H_2O$ (4:1, 4.95 ml) was added to conduit 16 at a rate of 9.90 ml h$^{-1}$ (110.0 mmol h$^{-1}$) and methyl trans-2-methyl pentenoate 24 (0.14 g, 1.09 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield methyl 3-ethyl-2-methyloxirane-2-carboxylate (0.16 g, 1.08 mmol, 99%) as a clear oil, with no further purification required;

$\delta_H$ (400 MHz, CDCl$_3$) 1.04 (3H, t, $^3J_{HH}$ 8, —CH$_2$CH$_3$), 1.49 (3H, s, CCH$_3$), 1.56 (2H, m, CH$_3$CH$_2$—), 3.12 (1H, t, $^3J_{HH}$ 8, —CH$_2$CH), 3.72 (3H, s, OCH$_3$); $\delta_C$ (100 MHz, CDCl$_3$) 10.2 (1C, s, C$_1$), 13.3 (1C, s, C$_4$), 21.4 (1C, s, C$_2$), 52.5 (1C, s, C$_7$), 57.6 (1C, s, C$_5$), 63.4 (1C, s, C$_3$), 172.0 (1C, s, C$_6$); m/z (EI) 144 (M$^+$, 14%).

1,3,4,6-tetramethyl-7-oxabicyclo[4.1.0]hept-3-ene-2,5-dione from duroquinone

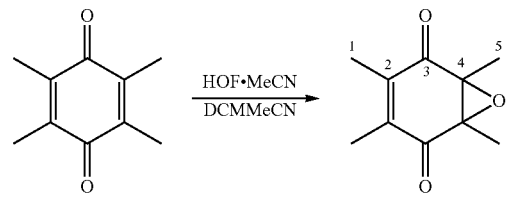

Under a flow of $F_2$ (10% in $N_2$) of 20.0 ml min$^{-1}$ (3.33 mmol h$^{-1}$) passed through first conduit 12, MeCN:$H_2O$ (4:1, 4.95 ml) was added to conduit 16 at a rate of 9.90 ml h$^{-1}$ (110.0 mmol h$^{-1}$) and duroquinone 24 (0.32 g, 1.95 mmol) (in a 1:1 mixture of DCM:MeCN) was added to conduit 38 at a rate of 9.90 ml h$^{-1}$. All reaction fluids were collected in a pot 22 containing sodium bicarbonate solution 25 (50 ml). The reaction mixture was then added to another 25 ml of sodium bicarbonate solution, washed with DCM (3×75 ml), dried over MgSO$_4$ and filtered. The solvent was removed under reduced pressure to yield a mixture of 2 products (0.34 g) (confirmed by GC) as yellow crystals which contained 1,3,4, 6-tetramethyl-7-oxabicyclo[4.1.0]hept-3-ene-2,5-dione (0.13 g, 0.74 mmol, 38%);

$\delta_H$ (400 MHz, CDCl$_3$) 1.6 (3H, s, —OCCH$_3$), 1.97 (3H, s, —C=CCH$_3$); $\delta_C$ (100 MHz, CDCl$_3$) 11.7 (2C, s, C$_1$), 13.5 (2C, s, C$_5$), 63.3 (2C, s, C$_4$), 141.1 (2C, s, C$_2$), 194.5 (2C, s, C$_3$); m/z (EI) 165 (M$^+$-CH$_3$, 8%).

Trans-5-decene was reacted with 1 equivalent of HOF.MeCN according to the method described above to yield 90% of the corresponding epoxide.

Ethyl-trans-cinnamate was reacted with 1 equivalent of HOF according to the method above to yield 39% epoxide and 61% of the alkene. This alkene is known to be unreactive and also has an aromatic ring which is a competing group. It was also reacted with 2 equivalents of HOF according to the above method and yielded 63% epoxide and 37% alkene. In the case of this substrate, the reaction products were identified by their $^1$H NMR and $^{13}$C{$^1$H} NMR spectra, and were not isolated.

Aromatic Amines

Phenylamine was oxidised with 3.6 equivalents of HOF.MeCN according to the method described above to yield 68% nitrobenzene.

Pentafluorophenyl amine was oxidised with 4.2 equivalents of HOF.MeCN according to the method described above to yield 35% pentafluoronitrobenzene. The low yield can be accounted for due to the electron deficiency of the amine requiring a longer residence time, which was not used in this case.

Aliphatic Amines

The following reactions with aliphatic amines were carried out according to the method detailed above. Unlike the reactions specified in the prior art, these reactions did not require the use of an HF scavenging agent.

1-aminohexane was reacted with 2.5 equivalents of HOF.MeCN to yield 81% of 1-nitrohexane 1-aminodecane was reacted with 4.2 equivalents of HOF.MeCN to yield 60% of 1-nitrodecane.

1-aminoadamantane was reacted with 4.2 equivalents of HOF.MeCN to yield 48% of 1-nitroadamantane.

1-amino-6-hexanol was reacted with 4.2 equivalents of HOF.MeCN to yield 41% of 1-nitro-6-hexanol.

Aminocyclohexane was reacted with 4.2 equivalents of HOF.MeCN to yield 30% of nitrocyclohexane Tertiary Nitrogen Centres Methoxypyrazine was reacted with 1 equivalent of HOF.MeCN to yield 80% of one of the corresponding N-oxides.

4-cyanopyridine was reacted with 1 equivalent of HOF.MeCN to yield 59% of 4-cyanopyridine-N-oxide.

Azides 1-azidooctane was reacted with 4.2 equivalents of HOF.MeCN to yield 35% of 1-nitrooctane and 65% unreacted starting material.

1-azidoadamantane was reacted with 4.2 equivalents of HOF.MeCN to yield 81% of 1-nitroadamantane.

Elevated Temperature Oxidations (Alkenes)

Ethyl-trans-cinnamate was reacted at 40° C. using the apparatus shown in FIG. 3 with 1 equivalent of HOF and yielded 49% epoxide and 51% alkene, showing an improvement on the ambient temperature reaction described above. It was also reacted with 2 equivalents of HOF according to the same method to yield 78% epoxide and 22% alkene.

This reaction is effected in seconds whereas the prior art specifies long reaction times and 3 equivalents of HOF to achieve an 85% yield. In the case of this substrate, the reaction products were identified by their $^1$H NMR and $^{13}$C{$^1$H} NMR spectra, and were not isolated.

Ethyl-trans-cinnamate was reacted at 60° C. using the apparatus shown in FIG. 3 with 1 equivalent of HOF to yield 51% epoxide and 49% alkene. It was also reacted with 2 equivalents of HOF according to the same method to yield 84% epoxide and 16% alkene. In the case of this substrate, the reaction products were identified by their $^1$H NMR and $^{13}$C{$^1$H} NMR spectra, and were not isolated.

All of these reactions were effected in quicker time and under much safer conditions than reported in the prior art.

The invention claimed is:

1. A process for oxidising a substrate using a microreactor having at least one channel comprising the steps of:
    passing diluted fluorine through a conduit into a microreactor channel;
    passing RCN in water through another conduit thereby forming HOF.RCN wherein R is methyl, ethyl, propyl, butyl or iso-butyl; and
    contacting the HOF.RCN with a substrate to be oxidised such that conversion of fluorine to HOF.RCN proceeds in a stoichiometric manner such that one equivalent of fluorine generates one equivalent of HOF.RCN, wherein the HOF.RCN formation and oxidation stages are decoupled within the same reaction system allowing the continuous generation of HOF.RCN thereby minimising degradation of the HOF.RCN prior to contact with the substrate and reducing or eliminating the exposure of the substrate to fluorine.

2. The process according to claim 1 wherein the substrate to be oxidised is contained in a pot reactor which is connected to the microreactor via a conduit.

3. The process according to claim 1 wherein HOF.RCN is flowed into a pot reactor which contains RCN via a conduit.

4. The process according to claim 3 wherein the substrate to be oxidised is added to the pot reactor after HOF.RCN generation.

5. The process according to claim 1 wherein the substrate to be oxidised is fed through a conduit to react with HOF.RCN generated in the said microreactor.

6. The process according to claim 1 wherein the substrate to be oxidised is fed into the said microreactor through a conduit after the fluorine and RCN/H$_2$O had been flowed in to the microreactor.

7. The process according to claim 1 wherein the reaction products collect in a pot reactor.

8. The process according to claim 7 wherein the pot reactor contains a quench solution.

9. The process according to claim 8 wherein the quench solution is NaHCO$_3$.

10. The process according to claim 1 wherein the fluorine is diluted in an inert gas.

11. The process according to claim 1 wherein the microreactor has a second channel through which a cooling fluid is passed to cool the said microreactor.

12. The process according to claim 1 wherein the said microreactor has a second channel through which a heating fluid is passed to heat the said microreactor.

13. The process according to claim 1 wherein the substrates are selected from the group consisting of: aliphatic amines, aromatic amines, alkenes, aliphatic azides and azaheterocycles.

14. The process according to claim 13 wherein the azaheterocycles are selected from the group consisting of: pyridines, pyrazines, pyridazines, triazines, tetrazenes, pyrimidines, quinolines, isoquinolines and quinoxalines.

* * * * *